(12) United States Patent
Philippe

(10) Patent No.: US 7,144,572 B2
(45) Date of Patent: Dec. 5, 2006

(54) USE OF POLYGUANIDINE COMPOUND FOR TREATING OR SHAPING THE HAIR, ESPECIALLY FOR STRAIGHTENING OR PERMANENT-WAVING IT

(75) Inventor: Michel Philippe, Wissous (FR)

(73) Assignee: L'Oreal, Paris (FR)

( * ) Notice: Subject to any disclaimer, the term of this patent is extended or adjusted under 35 U.S.C. 154(b) by 357 days.

(21) Appl. No.: 10/265,913

(22) Filed: Oct. 8, 2002

(65) Prior Publication Data

US 2003/0133898 A1 Jul. 17, 2003

(30) Foreign Application Priority Data

Oct. 9, 2001 (FR) .................................. 01 12973

(51) Int. Cl.
*A61Q 5/04* (2006.01)
(52) U.S. Cl. .................................. 424/70.2; 424/70.11
(58) Field of Classification Search .................... None
See application file for complete search history.

(56) References Cited

U.S. PATENT DOCUMENTS 5,932,201 A    8/1999   deLabbey et al. ....... 424/70.17

FOREIGN PATENT DOCUMENTS

| EP | 0 439 698 | 8/1991 |
| FR | 2 514 640 | 4/1983 |
| RU | 857 257 | 8/1981 |
| RU | 2 052 453 | 1/1996 |
| RU | 2 106 859 | 3/1998 |
| RU | 2 143 905 | 1/2000 |
| WO | WO 99 54291 | 10/1999 |

OTHER PUBLICATIONS

Harrys Cosmeticology, pp. 558-561 (1982).*

* cited by examiner

*Primary Examiner*—Jyothsna Venkat
(74) *Attorney, Agent, or Firm*—Steptoe & Johnson LLP

(57) ABSTRACT

The present invention relates to the use of a cosmetic composition containing compounds derived from polyguanidines or physiologically acceptable salts thereof for the protection of keratin fibres during permanent-shaping treatments or hair-straightening operations. The invention also relates to a cosmetic treatment process for permanently shaping or straightening keratin fibres, such that it consists in applying to these fibres a composition containing a compound derived from polyguanidines.

6 Claims, No Drawings

USE OF POLYGUANIDINE COMPOUND FOR TREATING OR SHAPING THE HAIR, ESPECIALLY FOR STRAIGHTENING OR PERMANENT-WAVING IT

The present invention relates to the use of polyguanidines or physiologically acceptable salts thereof for the protection of keratin fibres during permanent-shaping treatments or hair-straightening operations.

The invention also relates to a cosmetic treatment process for permanently shaping or straightening keratin fibres, such that it consists in applying to the keratin fibres a composition containing a compound derived from polyguanidines.

Polyalkylene guanidines are copolymers obtained by condensation of guanidine hydrochloride with an alkylenediamine. Such compounds and the preparations thereof from hexamethylenediamine have been known since 1975 by Zh. Prikl. Khim. (Leningrad) (1975), 48 (8), 1833–6, from Gembitskii, P. A. et al.

Polyalkylene guanidines are known for their antibacterial activity, and this use is especially described in patents RU 2 143 905 and SU 1 687 261. More recently, the use of polyalkylene guanidines for skin care has been described. Thus, patents SU 1 803 099 and RU 2 106 859 describe the cicatrizing and emollient properties of these compounds.

Patent application SU 857 257 describes the highly detergent properties of compositions based on polyhexamethylene guanidines.

Various processes are known for synthesizing these polyalkylene guanidine derivatives.

Patent applications EP 0 439 698, WO 99/54291 or RU 2 052 453 present alternatives to the processes for synthesizing polyalkylene guanidines described in the publication by Gembitskii et al. cited above.

Advantageously and surprisingly, the inventors have discovered that compounds derived from polyalkylene guanidines of formula (I) that will be defined below can be used in cosmetics to care for keratin fibres during permanent-shaping treatments.

Preferably, the compound derived from polyguanidines will form part of the reducing composition used during the permanent-shaping operation.

It is known that hair that is regularly subjected to permanent-waving operations loses its mechanical properties. This permanent-waved hair is more brittle and harder to shape, and furthermore it is difficult to obtain a uniform coloration on permanent-waved hair.

It has also been noted that cosmetic treatments intended to straighten keratin materials, and in particular the hair, also have the consequence of adversely affecting the mechanical properties of the keratin materials.

The inventors have thus shown that the use of compositions containing compounds derived from polyguanidines, during permanent-shaping or hair-straightening operations, makes it possible to limit or even nullify the degradative effects of permanent-waving operations.

The compounds derived from polyguanidine that may be used in the context of the present invention correspond to formula (I) below:

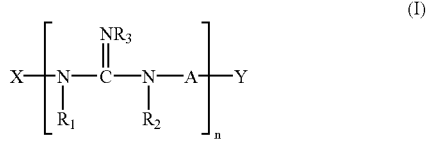

in which:

X, $R_1$, $R_2$ and $R_3$, independently of each other, are chosen from the group formed by a hydrogen atom, a hydroxyl radical and a linear or branched, saturated or unsaturated, optionally hydroxylated $C_1$ to $C_{16}$ and preferably $C_1$ to $C_8$ alkyl radical, Y denotes a radical NHR, in which R is chosen from the group formed by a hydrogen atom, a hydroxyl radical and a linear or branched, saturated or unsaturated, optionally hydroxylated $C_1$ to $C_{16}$ and preferably $C_1$ to $C_8$ alkyl radical, A denotes a linear or branched, saturated or unsaturated, $C_1$ to $C_{16}$ and preferably $C_1$ to $C_{12}$ alkylene radical optionally substituted with at least one radical chosen from a hydroxyl, carboxyl (—COOH) or carboxylate radical and a halogen, the said alkylene radical possibly containing at least one amine (—NH—), ether (—O—), thioether (—S—), ester (—(CO)O— or —O(CO)—), amide (—CONR— or —NRCO— in which R is hydrogen or a $C_1$ to $C_8$ alkyl radical), carbamate (—NH(CO)O— or —O(CO)NH—) or urea (—NH(CO)NH—) function, a $C_6$ aryl or $C_3$ to $C_8$ cyclanyl ring optionally substituted with a $C_1$–$C_8$ alkyl, hydroxyl or halogen; or A denotes one or more $C_6$ or $C_7$ aryl or $C_5$ to $C_7$ cyclanyl rings optionally substituted with a $C_1$–$C_8$ alkyl, a hydroxyl group or a halogen or are unsubstituted; or A denotes a $C_{10}$ to $C_{14}$ polyaryl or $C_6$ to $C_{10}$ polycyclanyl chain, which may be interrupted with at least one $C_1$ to $C_8$ alkylene radical, an amine (—NH—), amide (—CONR— or NRCO in which R is a $C_1$ to $C_8$ alkyl radical), ether (—O—), thioether (—S—), a hydrogen atom, carbamate (—NH(CO)O— or —O(CO)NH—) or urea (—NH(CO)NH—) function;

n is an integer between 2 and 5 000 and preferably between 2 and 200, and the physiologically acceptable salts thereof.

For the purposes of the present patent application, the term "carboxylate" means an addition salt of a carboxylic acid with a base chosen especially from sodium hydroxide, potassium hydroxide, aqueous ammonia, amines or alkanolamines or alternatively an ampholytic internal salt with a guanidinium group of the chain.

For the purposes of the present patent application, the expression "$C_6$ aryl ring" means a benzene nucleus, this nucleus possibly being substituted with one or two $C_1$ or $C_8$ alkyl radicals, OH or halogen.

For the purposes of the present patent application, the expression "$C_{10}$ to $C_{14}$ polyaryl chain" means a chain containing 2 or 3 aromatic nuclei, each optionally being substituted with one or two $C_1$ to $C_8$ alkyl radicals, OH or halogen.

Preferably, they will more particularly be derivatives of formula (I) defined above, in which A denotes a linear or branched, saturated or unsaturated $C_1$ to $C_6$ alkylene radical, optionally substituted with at least one radical chosen from hydroxyl, carboxyl and carboxylate radicals or halogens (fluorine, chlorine, bromine or iodine).

As compounds derived from polyguanidines, either homopolymers or heteropolymers may be used.

For the purposes of the present patent application, the term "homopolymer" means a polymer chain consisting of (—N($R_1$)—C(N$R_3$)—N($R_2$)-A) units, in which $R_1$, $R_2$, $R_3$ and A are always identical, and the term "heteropolymer" means a polymer for which at least one of the units $R_1$, $R_2$, $R_3$ and A is different from the others.

Even more preferably, the compounds used in the compositions for protecting and/or caring for keratin fibres, within the meaning of the present invention, are polytetramethyleneguanidinium and polyhexamethyleneguanidinium salts and more particularly the halides (fluoride, chloride and bromide), the carboxylates (gluconates, acetates and lactates) or an ampholytic internal salt with a guanidinium group of the chain; it will preferably be polyhexamethyleneguanidinium chloride, polytetramethyleneguanidinium chloride or polytetramethyleneguanidinium acetate.

The polyguanidine derivatives that may be used in the context of the present invention may be prepared by carrying out any preparation process known in the prior art. In particular, the compounds derived from polyguanidine according to the present invention are prepared by mixing an alkylenediamine and a guanidine salt, for example guanidine hydrochloride, in an approximately equimolar ratio, followed by heating this mixture to a temperature of between 120 and 150° C. for a period of between 4 and 10 hours. The alkylenediamine and the guanidine salt may be mixed together in bulk in the presence of a solvent, which will preferably be polyethylene glycol (PEG).

PEG has the advantage of being a good solvent for the reagents: alkylenediamine and guanidine salt; on the other hand, the compound derived from polyguanidine obtained after the reaction is immiscible with PEG. This process thus makes it possible to recover the compound derived from polyguanidine directly and also to recover the PEG, which may be reused as solvent, and also the excess reagents or reagents that have not had time to react.

According to another variant of the process for preparing the compounds derived from polyguanidines according to the invention, the heating step may be carried out in two stages: a first step of heating at a temperature of between 80 and 120° C., and preferably at about 120° C., for a period of between 4 and 5 hours, followed by a second step of heating at a temperature of between 120 and 160° C., and preferably at about 150° C., for a period of between 8 and 11 hours.

The process of Gembitskii et al., cited above, and also the processes described in patent applications WO 99/54291 and EP 439 698 may be used to prepare the compounds derived from polyguanidines according to the present invention.

One subject of the present patent application is a cosmetic composition comprising a combination of at least one polyguanidine derivative of formula (I) or a physiologically acceptable salt thereof and a compound chosen from keratin-reducing compounds and keratin-fixing compounds.

The present patent application also relates to the use of this cosmetic composition for carrying out a permanent-shaping or straightening of the hair, and it may be a reducing composition or a fixing composition, which is preferably oxidative.

The present application also relates to a multi-compartment device or "kit" such that one of the compartments comprises a reducing composition containing a combination of a compound derived from polyguanidine and a keratin-reducing compound and a multi-compartment device or "kit" such that one of the compartments comprises a fixing composition containing a combination of a compound derived from polyguanidine and a keratin-fixing compound.

Another subject of the present invention comprises a cosmetic treatment process for permanently shaping or straightening keratin fibres, in particular the hair, such that it consists in applying to these fibres a cosmetic composition comprising the combination of a compound derived from polyguanidine or a physiologically acceptable salt thereof and a compound chosen from keratin-reducing compounds and keratin-fixing compounds.

The polyguanidine derivative may be used in combination with any keratin-reducing compound or with any keratin-fixing compound that is standard in any standard cosmetic composition for carrying out a permanent-waving or hair-straightening operation.

Preferably, the compounds derived from polyguanidine of formula (I) will be used for or in reducing compositions for carrying out permanent-waving operations or for carrying out a hair-straightening operation.

The reducing compositions for carrying out permanent-waving operations may consist of any composition already known per se as a reducing composition.

More particularly, the reducing compositions that may be used to carry out permanent-waving operations contain, as keratin-reducing agents, sulphites/or bisulphites, especially of alkali metals, of alkaline-earth metals or of ammonium or, preferably, thiols. Among the thiols, those that are most commonly used are cysteine and its various derivatives (especially N-acetylcysteine), cysteamine and its various derivatives (especially its $C_1$–$C_4$ acyl derivatives such as N-acetylcysteamine or N-propionyl-cysteamine), thiolactic acid and its esters (especially glyceryl monothiolactate), thioglycolic acid and its esters, especially glyceryl or glycol monothioglycolate, and thioglycerol. Mention may also be made of the following reducing agents: N-mercaptoalkylamides of sugars, such as N-(2-mercaptoethyl)gluconamide, β-mercaptopropionic acid and its derivatives, thiomalic acid, pantethine, the N-(mercaptoalkyl)-ω-hydroxyalkylamides described in patent application EP-A-354 835 and the N-mono- or N,N-dialkylmercapto 4-butyramides described in patent application EP-A-368 763, the aminomercaptoalkylamides described in patent application EP-A-432 000 and the alkylamino-mercaptoalkylamides described in patent application EP-A-514 282, the mixture of 2-hydroxypropyl thioglycolate (2/3) and of 2-hydroxy-1-methylethyl thioglycolate (67/33) described in patent application FR-A-2 679 448.

These keratin-reducing agents are generally used in cosmetically acceptable compositions, which are moreover already well known per se in the existing prior art of curling formulations for performing the first step (reduction) of a permanent-waving operation. Thus, as common and standard additives, that may be used alone or as a mixture, mention may be made more particularly of surfactants of nonionic, anionic, cationic or amphoteric type, and among these mention may be made of alkyl sulphates, alkylbenzene sulphates, alkyl ether sulphates, alkyl sulphonates, quaternary ammonium salts, alkylbetaines, oxyethylenated alkylphenols, fatty acid alkanolamides, oxyethylenated fatty acid esters and also other nonionic surfactants of the hydroxypropyl ether type.

When the reducing composition contains at least one surfactant, this surfactant is generally present in a maximum concentration of 30% by weight and preferably between 0.5% and 10% by weight relative to the total weight of the reducing composition.

With the aim of improving the cosmetic properties of the hair or of attenuating or preventing its degradation, the reducing composition may also contain, in addition to the compound derived from polyguanidine, a treating agent of cationic, anionic, nonionic or amphoteric nature.

Among the treating agents that are particularly preferred, mention may be made especially of those described in French patent applications Nos. 2 598 613 and 2 470 596. Treating agents that may also be used include volatile or non-volatile, linear or cyclic silicones and mixtures thereof, polydimethylsiloxanes, quaternized polyorganosiloxanes such as those described in French patent application No. 2 535 730, polyorganosiloxanes containing aminoalkyl groups modified with alkoxycarbonylalkyl groups, such as those described in U.S. Pat. No. 4,749,732, polyorganosiloxanes such as polydimethylsiloxane-polyoxyalkyl copolymer of the Dimethicone Copolyol type, a polydimethylsiloxane containing stearoxy(stearoxydimethicone) end groups, a polydimethylsiloxanedialkylammonium acetate copolymer or a polydimethylsiloxane polyalkylbetaine copolymer described in British patent application No. 2 197 352, polysiloxanes organomodified with mercapto or mercaptoalkyl groups such as those described in French patent No. 1 530 369 and in European patent application No. 295 780, and also silanes such as stearoxy-trimethylsilane.

The reducing composition may also contain other treating ingredients such as cationic polymers, such as those used in the compositions of French patents Nos. 79/32078 (FR-A-2 472 382) and 80/26421 (FR-A-2 495 931), or cationic polymers of the ionene type, such as those used in the compositions of the Luxembourg patent No. 83703, basic amino acids (such as lysine or arginine) or acidic amino acids (such as glutamic acid or aspartic acid), peptides and derivatives thereof, protein hydrolysates, waxes, swelling and penetrating agents or agents for reinforcing the efficacy of the reducing agent, such as the $SiO_2$/PDMS (polydimethylsiloxane) mixture, dimethylisosorbitol, urea and its derivatives, pyrrolidone, N-alkylpyrrolidones, thiamorpholinone, alkylene glycol or dialkylene glycol alkyl ethers such as, for example, propylene glycol monomethyl ether, dipropylene glycol monomethyl ether, ethylene glycol monoethyl ether and diethylene glycol monoethyl ether, $C_3$–$C_6$ alkanediols such as, for example, 1,2-propanediol and 1,2-butanediol, 2-imidazolidinone, and also other compounds such as fatty alcohols, lanolin derivatives, active ingredients such as pantothenic acid, agents for preventing hair loss, antidandruff agents, thickeners, suspension agents, sequestering agents, opacifiers, colorants, sunscreens, and also fragrances and preserving agents.

In permanent-wave reducing compositions, the reducing agents such as those mentioned above are generally present in a concentration which may be between 1% and 30% by weight and preferably between 5% and 20% by weight relative to the total weight of the reducing composition.

The reducing composition may be in the form of a thickened or unthickened lotion, a cream, a gel or in any other suitable form.

The reducing composition may also be of the exothermic type, i.e. causing a certain amount of heating when applied to the hair, which provides a pleasant sensation to the individual on whom the permanent-waving or hair-straightening operation is being performed.

The reducing composition may also contain a solvent such as, for example, ethanol, propanol or isopropanol, or alternatively glycerol at a maximum concentration of 20% relative to the total weight of the composition.

The vehicle for the compositions is preferably water or an aqueous-alcoholic solution of a lower alcohol such as ethanol, isopropanol or butanol.

When the compositions are intended for a straightening or curl-removing operation on the hair, the reducing composition is preferably in the form of a thickened cream, so as to keep the hair as straight as possible. These creams are produced in the form of "heavy" emulsions.

For example, in order to obtain a cream, an aqueous phase containing, in solution, the compound derived from polyguanidines and optionally other ingredients or adjuvants, and an oily phase, may be emulsified.

The oily phase may consist of various products, such as liquid paraffin, liquid petroleum jelly, sweet almond oil, avocado oil, olive oil, fatty acid esters, for instance glyceryl monostearate, ethyl or isopropyl palmitate, and alkyl myristates, such as propyl, butyl or cetyl myristate. Fatty alcohols, for instance cetyl alcohol, or waxes such as, for example, beeswax may also be added.

Liquids or gels containing thickeners such as carboxyvinyl polymers or copolymers which "stick" the hair together and keep it in the smooth position during the application time, may also be used.

Finally, the reducing compositions may also contain at least one disulphide known for its use in a self-neutralizing reducing composition for permanent-waving.

Among such known disulphides, mention may be made especially of dithioglycolic acid, dithioglycerol, cystamine, N,N'-diacetylcystamine, cystine, pantethine, and the N-(mercaptoalkyl)-ω-hydroxyalkylamide disulphides described in European patent application EP 354 835, the N-mono- or N,N-dialkylmercapto-4-butyramide disulphides described in patent application EP 368 763, the aminomercaptoalkylamide disulphides described in patent application EP 432 000, and the alkylaminomercaptoalkylamide disulphides described in patent application EP 514 282. These disulphides are generally present in a molar ratio of from 0.5 to 2.5 and preferably from 1 to 2 relative to the reducing agent (see patent U.S. Pat. No. 3,768,490).

The pH values of the reducing compositions may be conventionally adjusted by adding either basifying agents such as, for example, aqueous ammonia, monoethanolamine, diethanolamine, triethanolamine, isopropanolamine, 1,3-propanediamine, an alkali metal or ammonium carbonate or bicarbonate, an organic carbonate such as guanidine carbonate (carbonated reducing compositions) or an alkali metal hydroxide, it obviously being possible for all these compounds to be taken alone or as a mixture, or acidifying agents such as, for example, hydrochloric acid, acetic acid, lactic acid or boric acid.

The compositions comprising, in combination, at least one polyguanidine derivative of formula (I) and at least one reducing compound chosen from the sulphites and bisulphites as defined above may be applied repeatedly to the hair to carry out permanent-waving or hair-straightening operations, without any major change in the behaviour of this hair being observed, in particular as regards its ability to be correctly coloured thereafter.

Specifically, it is generally observed that, on hair that has undergone a number of permanent-waving or straightening operations (of the order of three at most), the coloration will be much more pronounced than that obtained on the same hair, but which is not permanent-waved. This therefore poses a problem in all cases in which the colouring operation is performed on a head of hair that was originally permanent-waved, but that has grown in the intervening time (poor unison between the original permanent-waved hair and the non-permanent-waved new hair growth).

It is also observed that colouring becomes very difficult, or even impossible, if the head of hair to be coloured has previously undergone several permanent-waving or straightening operations, in particular more than five permanent-waving operations.

It should be pointed out that the cosmetic compositions used in the context of the invention are both ready-to-use compositions and concentrates that need to be diluted before use. The cosmetic compositions are therefore not limited to a particular concentration range of the compounds derived from polyguanidines.

Generally, in the cosmetic compositions used, the concentration of compounds derived from polyguanidines is between 0.001% and 25% by weight and preferably between 0.1% and 10% by weight relative to the total weight of the composition.

EXAMPLES

I Fibre-Protecting Effect

With the aim of evaluating their protective properties on keratin fibres, compositions containing a polyguanidine derivative were subjected to a test of "diametral swelling in a liquid".

Without wishing to be bound to any theory, this test is based on the following principle: the diameter of the hair increases in water, and this swelling depends, inter alia, on the sensitivity of the hair. The increase stabilizes after a few minutes. Thus, the more sensitized the hair, i.e., the more degraded, the more its diameter will increase when it is placed in a liquid.

It has also been observed that there is additional swelling in the reduction phase during a permanent-waving operation. Without wishing to be bound to any theory, this swelling appears to be the consequence of breakage of the disulphide bridges and the generation of thiolates. This swelling stabilizes about 8 minutes after the start of the reduction phase.

It has also been observed that there is additional overswelling when the hair fibre is rinsed with deionized water. Without wishing to be bound to any theory, this overswelling appears to be due to osmotic shock, to the electrostatic repulsion between the chains of the hair fibres.

The following measurements were taken using a contactless Zimmer optical measuring system. According to this system, a hair is suspended in a quartz cuvette, into which the various treatment liquids are successively introduced. The change in the diameter of the fibre is recorded continuously during the various treatment phases. The results are obtained from 4 to 7 tests for each treatment performed.

The swelling test in permanent-waving medium is especially described in the following publications:

(1) J. Nothen "Proceedings" 16th IFSCC Congress 1990, page 315;

(2) A. Schansky "Journal of Society of Cosmetic Chemist" Vol. 14, 1963, page 427; and (3) K. W. Herrmann "Transation Faraday Society" Vol. 59, p. 1663, year 1963.

COMPARATIVE EXAMPLES

Bleached hairs are treated separately using three reducing solutions, $Red_1$, $Red_2$ and $Red_3$, and then rinsed. The change in the diametral swelling is measured during the reduction phase and during rinsing. The progress of these tests and also the results are presented below.

The overswelling corresponds to the difference between the start of swelling during rinsing (at T+13) and the end of swelling in the reducing agent (at T+11).

$Red_1$ is a thioglycolic acid (TGA) solution at 7% by weight brought to pH 8 with aqueous ammonia.

$Red_2$ is a thioglycolic acid solution at 7% by weight brought to pH 8 with aqueous ammonia and comprising 1 g of polyhexamethyleneguanidinium chloride.

$Red_3$ is a glycolic acid solution at 7% by weight brought to pH 8 using aqueous ammonia and comprising 1% by weight of polytetramethylene-guanidinium chloride.

For the test, the following treatments are successively carried out on the hair:

(1) distilled water for 2 minutes (T+2);
(2) reducing solution for 9 minutes (T+11);
(3) distilled water for 2 minutes (T+13); and
(4) distilled water for 2 minutes (T+15).

| Reduction phase | End of swelling in the reducing agent (%) at T + 11 | Start of swelling during rinsing (%) at T + 13 | End of swelling during rinsing (%) at T + 15 | Over-swelling (%) |
|---|---|---|---|---|
| $Red_1$ | 22.9 | 32.6 | 35.8 | 9.7 |
| $Red_2$ | 23.15 | 26.28 | 16.33 | 3.15 |
| $Red_3$ | 14.84 | 10.46 | 6.6 | −4.37 |

This test simulates the increase in the over-swelling of keratin fibres during a permanent-waving operation.

This test shows the efficacy of polytetra-methyleneguanidinium chloride and of polyhexamethylene-guanidinium chloride as fibre-protecting agents in reducing compositions that may be used during permanent-waving operations.

The composition based on polytetramethylene-guanidine chloride allows even a reduction in the overswelling of the fibre that is generally observed in the reduction phase of a permanent-waving operation.

II Examples of Permanent-Waving Compositions

Reducing Composition 1 (by Weight):

| | |
|---|---|
| Polyhexamethyleneguanidinium chloride | 1% |
| Thioglycolic acid | 8% |
| Monoethanolamine | qs pH 7 |
| Water | qs 100 |

| | |
|---|---|
| Polyhexamethyleneguanidinium chloride | 5% |
| Glyceryl monothioglycolate as a solution at 68% by weight in glycerol | 8% |
| Monoethanolamine | qs pH 7 |
| Water | qs 100 |

Reducing Composition 2 (by Weight):

The invention claimed is:

1. A method for permanent-shaping or straightening keratin fibres, comprising applying a cosmetic composition to the keratin fibers, the composition comprising a combination of a keratin-treating effective amount of a compound derived from polyguanidine of formula (I):

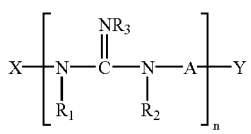

in which:
- X, $R_1$, $R_2$, $R_3$, independently of each other, are a hydrogen atom, a hydroxyl radical or a linear or branched, saturated or unsaturated, optionally hydroxylated $C_1$ to $C_{16}$ alkyl radical,
- Y denotes a radical NHR, in which R is a hydrogen atom, a hydroxyl radical or a linear or branched, saturated or unsaturated, optionally hydroxylated $C_1$ to $C_{16}$ alkyl radical,
- A denotes a linear or branched, saturated or unsaturated, $C_1$ to $C_{16}$ alkylene radical optionally substituted with at least one radical which is a hydroxyl, carboxyl or carboxylate radical or a halogen, the alkylene radical optionally containing at least one amine, ether, thioether, ester, amide, carbamate or urea function, a $C_6$ aryl or $C_3$ to $C_8$ cyclanyl ring optionally substituted with a $C_1$–$C_8$ alkyl, hydroxyl or halogen; or A denotes one or more $C_6$ or $C_7$ aryl or $C_5$ to $C_7$ cyclanyl rings unsubstituted or substituted with a $C_1$–$C_8$ alkyl, a hydroxyl group or a halogen; or A denotes a $C_{10}$ to $C_{14}$ polyaryl or $C_6$ to $C_{10}$ polycyclanyl chain, which may be interrupted with at least one $C_1$ to $C_8$ alkylene radical, an amine, amide, ether, thioether, a hydrogen atom, carbamate or urea function;
- n is an integer between 2 and 5000, or a physiologically acceptable salt thereof, and a keratin-reducing compound or keratin-fixing compound.

2. The method of claim 1, wherein the cosmetic composition is a reducing composition.

3. The method of claim 1, wherein the cosmetic composition is a fixing composition for carrying out a permanent-shaping of the keratin fibres.

4. The method of claim 1, wherein the polyguanidine compound represents from 0.001% to 25% by weight relative to the total weight of the cosmetic composition.

5. The method of claim 4, wherein the polyguanidine compound represents from 0.1 to 10% by weight relative to the total weight of the cosmetic composition.

6. The method of claim 1, wherein the cosmetic composition contains at least one nonionic, anionic, cationic or amphoteric surfactant, or nonionic, anionic, cationic or amphoteric treating agent.

* * * * *